US011242366B2

(12) United States Patent
Han et al.

(10) Patent No.: US 11,242,366 B2
(45) Date of Patent: Feb. 8, 2022

(54) MICROCAPSULE INCLUDING PEPTIDE HAVING CELL RECEPTOR BINDING AFFINITY AND COSMETIC COMPOSITION CONTAINING SAME

(71) Applicant: KOLMAR KOREA CO., LTD., Sejong-si (KR)

(72) Inventors: Sang Keun Han, Chungcheongnam-do (KR); Hyun Sook Lee, Sejong-si (KR); Eun Ah Kim, Sejong-si (KR); Seung Min Hyun, Gyeonggi-do (KR); Hyeong Choi, Sejong-si (KR); So Yoon Baek, Sejong-si (KR); Jae Hwa Hong, Sejong-si (KR); Chae Mi Lim, Seoul (KR); Da Jeong Bak, Seoul (KR); Hye Jin Jo, Seoul (KR); Hak Sung Lee, Chungcheongbuk-do (KR); Ji Hun Park, Gyeonggi-do (KR); Eun Young Lee, Sejong-si (KR)

(73) Assignee: KOLMAR KOREA CO., LTD., Sejong-si (KR)

( * ) Notice: Subject to any disclaimer, the term of this patent is extended or adjusted under 35 U.S.C. 154(b) by 0 days.

(21) Appl. No.: 16/636,458

(22) PCT Filed: Jan. 19, 2018

(86) PCT No.: PCT/KR2018/000916
§ 371 (c)(1),
(2) Date: Feb. 4, 2020

(87) PCT Pub. No.: WO2019/039676
PCT Pub. Date: Feb. 28, 2019

(65) Prior Publication Data
US 2020/0190143 A1 Jun. 18, 2020

(30) Foreign Application Priority Data

Aug. 24, 2017 (KR) .................. 10-2017-0107511
Jan. 17, 2018 (KR) .................. 10-2018-0006114

(51) Int. Cl.
| | |
|---|---|
| C07K 7/06 | (2006.01) |
| A61K 8/11 | (2006.01) |
| A61K 8/64 | (2006.01) |
| A61Q 19/00 | (2006.01) |
| A61Q 19/02 | (2006.01) |
| A61Q 19/08 | (2006.01) |
| C07K 5/103 | (2006.01) |
| A61K 38/00 | (2006.01) |
| A61K 45/06 | (2006.01) |

(52) U.S. Cl.
CPC .............. *C07K 7/06* (2013.01); *A61K 8/11* (2013.01); *A61K 8/64* (2013.01); *A61Q 19/007* (2013.01); *A61Q 19/02* (2013.01); *A61Q 19/08* (2013.01); *C07K 5/1008* (2013.01); *A61K 38/00* (2013.01); *A61K 45/06* (2013.01)

(58) Field of Classification Search
CPC ....................................................... A61K 8/11
See application file for complete search history.

(56) References Cited

U.S. PATENT DOCUMENTS

| | | | |
|---|---|---|---|
| 7,368,432 B2 | 5/2008 | McIntosh et al. | |
| 2011/0016545 A1* | 1/2011 | Gray | A01K 67/027 800/15 |
| 2013/0202740 A1 | 8/2013 | Given, Jr. et al. | |
| 2014/0112873 A1 | 4/2014 | Gillies et al. | |
| 2015/0238631 A1* | 8/2015 | Kim | A61K 47/48 |
| 2016/0206692 A1 | 7/2016 | Cochran et al. | |
| 2016/0250128 A1 | 9/2016 | Mourelle Mancini et al. | |
| 2016/0370372 A1* | 12/2016 | Koomen | G01N 33/574 |
| 2018/0207228 A1* | 7/2018 | Lundegaard | A61K 38/10 |

FOREIGN PATENT DOCUMENTS

| | | | |
|---|---|---|---|
| CN | 102296101 A | 12/2011 | |
| FR | 2885803 A1 * | 11/2006 | ............... A61Q 1/02 |
| JP | 2010220611 A | 10/2010 | |
| KR | 10-2006-0014444 A | 2/2006 | |
| KR | 10-1051557 B1 | 7/2011 | |
| RU | 2591454 C2 | 7/2016 | |
| WO | WO 00/03245 A1 | 1/2000 | |
| WO | WO 2000/003245 A1 | 1/2000 | |
| WO | 2010/083179 A2 | 7/2010 | |

OTHER PUBLICATIONS

Daniela S. Ferreira, Peptide-based microcapsules obtained by self-assembly and microfluidics as controlled environments for cell culture, Soft Matter, 2013, 9, 9237-9248 (Year: 2013).*

(Continued)

*Primary Examiner* — Mark V Stevens
*Assistant Examiner* — Alparslan Asan
(74) *Attorney, Agent, or Firm* — The PL Law Group, PLLC

(57) ABSTRACT

According to aspects of the present invention, a peptide with any one sequence of SEQ ID NOS:1 to 3 exhibits high selective binding affinity to a target and the microcapsule has superior physicochemical stability. Therefore, the cosmetic composition containing the microcapsule linked to the peptide manifests high delivery efficiency of an active ingredient included in the capsule to target cells, thereby exhibiting superior skin-condition improvement effects.

16 Claims, 15 Drawing Sheets

Specification includes a Sequence Listing.

(56) References Cited

OTHER PUBLICATIONS

FR2885803A1, Google English Translation, downloaded in Mar. 2021 (Year: 2021).*
Examination Report dated Jul. 24, 2020 from Australia Intellectual Property Office in a counterpart Australian Patent Application No. 2018320089 (all the cited references are listed in this IDS.).
International Search Report for PCT/KR2018/000916 dated May 31, 2018.
Office action dated Mar. 2, 2021 from Japan Intellectual Property Office in a counterpart Japanese Patent Application No. 2020-530295 (all the cited references are listed in this IDS.).
Alexander N. Plotnikov, et al. "Crystal Structures of Two FGF-FGFR Complexes Reveal the Determinants of Ligand-Receptor Specificity" Cell, 2000, vol. 101, pp. 413-424.

* cited by examiner

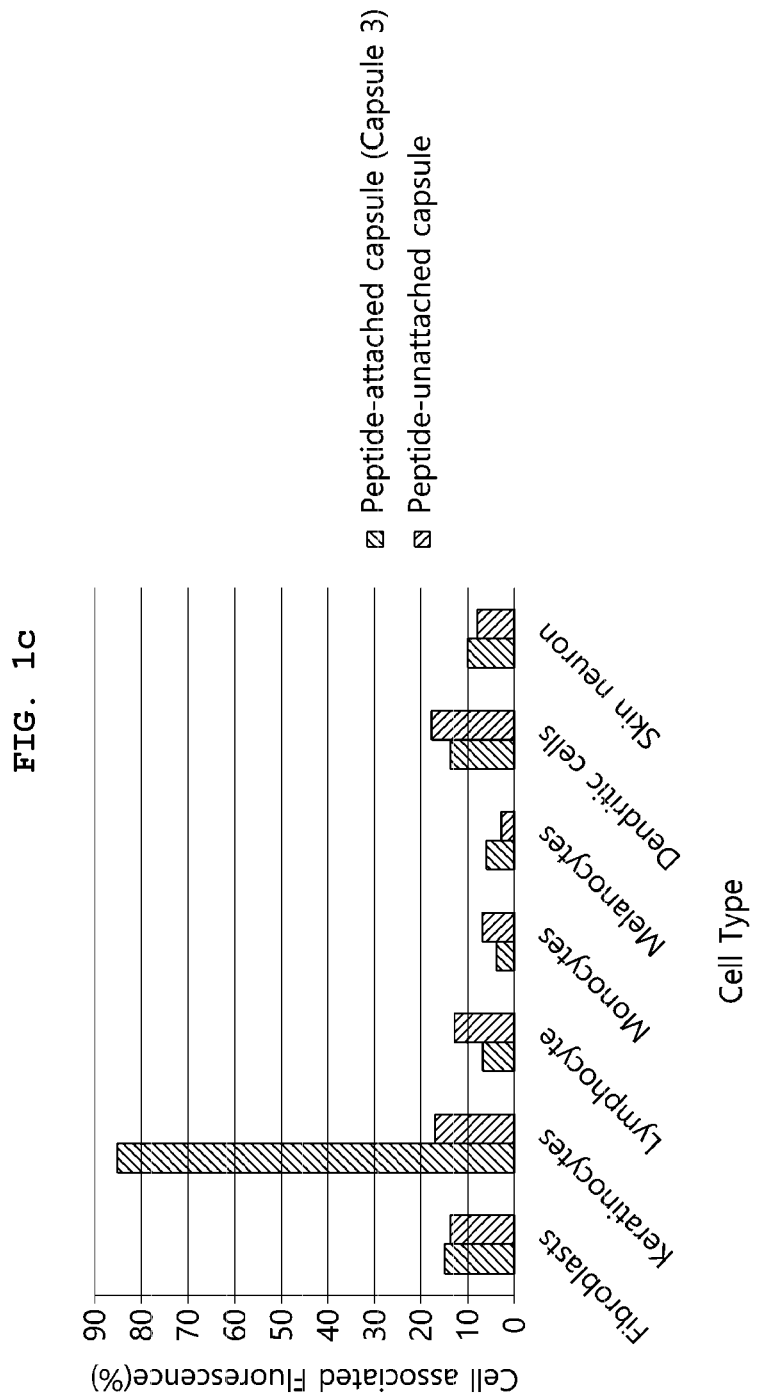

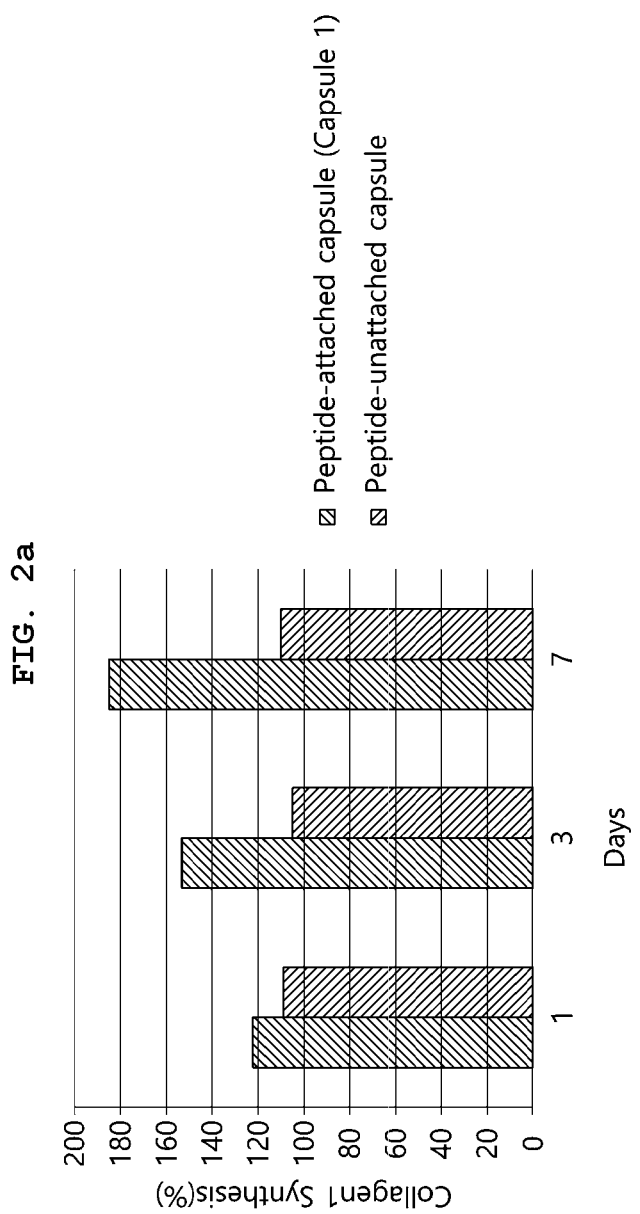

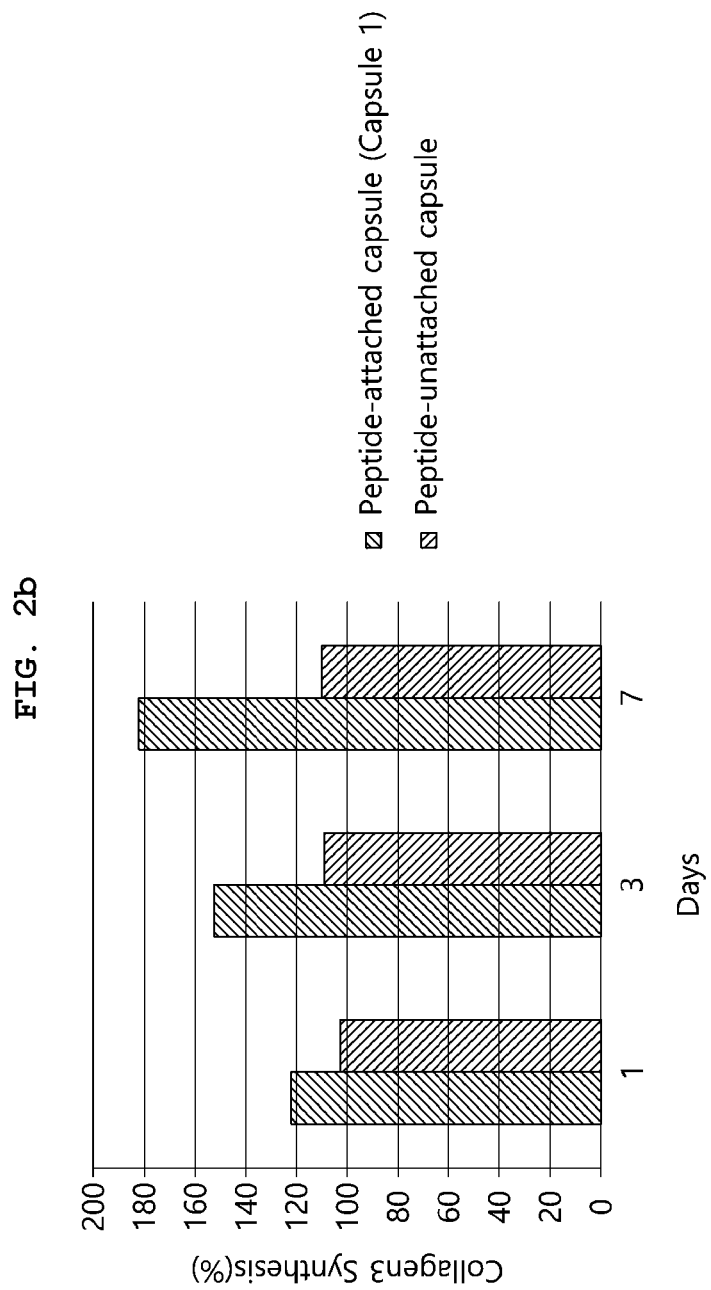

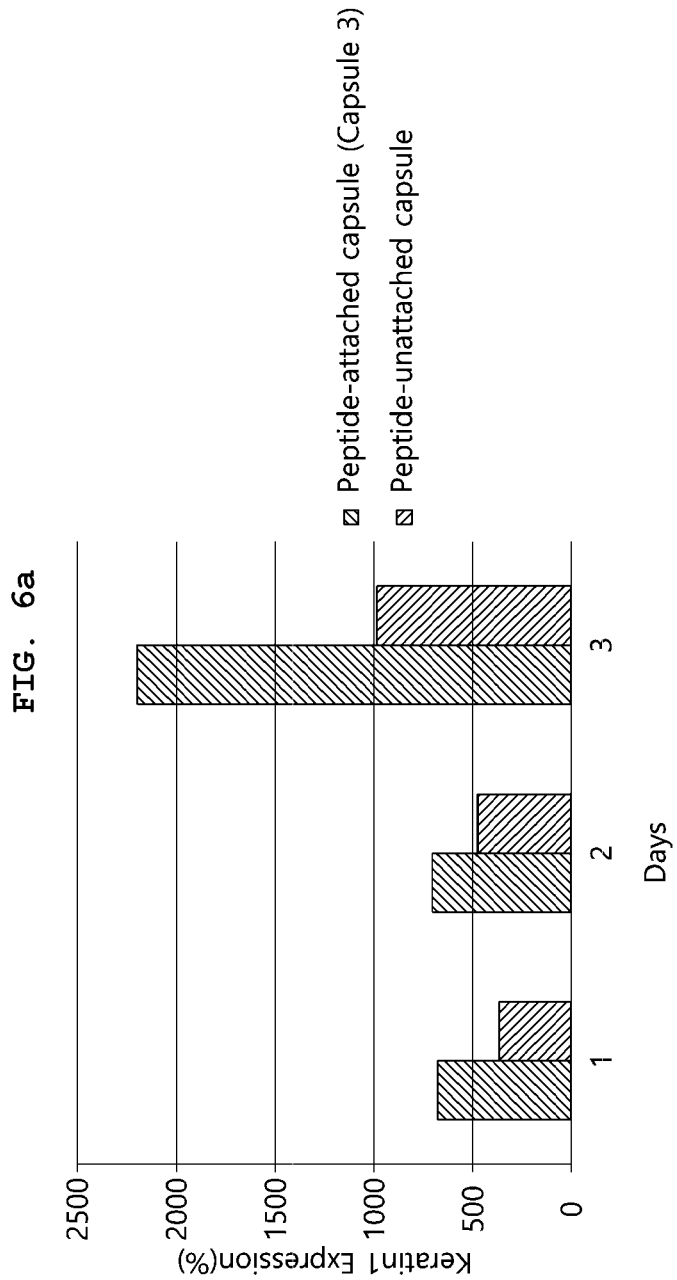

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: peptide of binding to fibroblast

<400> SEQUENCE: 1

Ala Lys Ser Thr
1

<210> SEQ ID NO 2
<211> LENGTH: 10
<212> TYPE: PRT
<213> ORGANISM: Artificial Sequence
<220> FEATURE:
<223> OTHER INFORMATION: peptide of binding to fibroblast

<400> SEQUENCE: 2

Glu Gly His Lys Ile Phe Pro Ser Trp Tyr
1               5                   10

<210> SEQ ID NO 3
<211> LENGTH: 5
<212> TYPE: PRT
<213> ORGANISM: Artificial Sequence
<220> FEATURE:
<223> OTHER INFORMATION: peptide of binding to keratinocytes

<400> SEQUENCE: 3

Ala Asp Gly Ser Pro
1               5
```

MICROCAPSULE INCLUDING PEPTIDE HAVING CELL RECEPTOR BINDING AFFINITY AND COSMETIC COMPOSITION CONTAINING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/000916, filed Jan. 19, 2018 which claims priority to the benefit of Korean Patent Application Nos. 10-2017-0107511 filed on Aug. 24, 2017 and 10-2018-0006114 filed on Jan. 17, 2018 in the Korean Intellectual Property Office, the entire contents of which are incorporated herein by reference.

TECHNICAL FIELD

The present invention relates to a peptide having binding ability to cell-receptor, a microcapsule including the peptide linked thereto, and a cosmetic composition containing the microcapsule.

BACKGROUND ART

A microcapsule is a base technology used in various fields, such as those of pharmaceuticals, paints, electronics and cosmetics, and is particularly receiving attention in the pharmaceutical and cosmetic fields as the best tool for maintaining the initial titer of an active ingredient (Journal of Controlled Release, 58, 9, 1999).

However, when applied to the human body, a cosmetic composition containing the microcapsule known at present does not exhibit a noticeably improved effect compared to a cosmetic composition not using the microcapsule.

Recently, development of delivering the microcapsule to target cells based on the drug delivery system principle is continuing. However, techniques known at present are still unsatisfactory due to the molecular instability of the microcapsule, problems related to binding affinity to target cells, and the like.

SUMMARY

An objective of the present invention is to provide a peptide having high binding affinity to target cells.

Another objective of the present invention is to accurately and stably deliver an active ingredient to target cells.

Still another objective of the present invention is to provide a cosmetic composition having improved delivery efficiency of an active ingredient to the skin.

An aspect of the present invention provides a peptide having binding ability to cell-receptor, in which the peptide includes any one sequence of SEQ ID NOS: 1 to 3.

Another aspect of the present invention provides a microcapsule including the peptide linked to the surface thereof.

Still another aspect of the present invention provides a cosmetic composition containing the microcapsule.

According to an aspect of the present invention, a peptide has superior selective binding affinity to a target. According to another aspect of the present invention, a microcapsule has superior physicochemical stability. Therefore, a cosmetic composition containing the microcapsule bound to the peptide can exhibit high delivery efficiency of an active ingredient included in the capsule to target cells, thereby manifesting superior skin-condition improvement effects.

BRIEF DESCRIPTION OF THE DRAWINGS

FIGS. 1a to 1c show the results of measurement of binding affinity of a capsule of the present invention to a target (target cells) (FIG. 1a: capsule 1, FIG. 1b: capsule 2, FIG. 1c: capsule 3).

FIGS. 2a to 2c show changes in expression of collagen 1 (FIG. 2a), collagen 2 (FIG. 2b) and elastin (FIG. 2c) upon treatment with capsule 1 of the present invention.

FIGS. 6a to 6c show changes in expression of keratin 1 (FIG. 6a), keratin 5 (FIG. 6b), and filaggrin (FIG. 6C) upon treatment with the capsule (capsule 3) of the present invention.

DETAILED DESCRIPTION

Figure 1A:
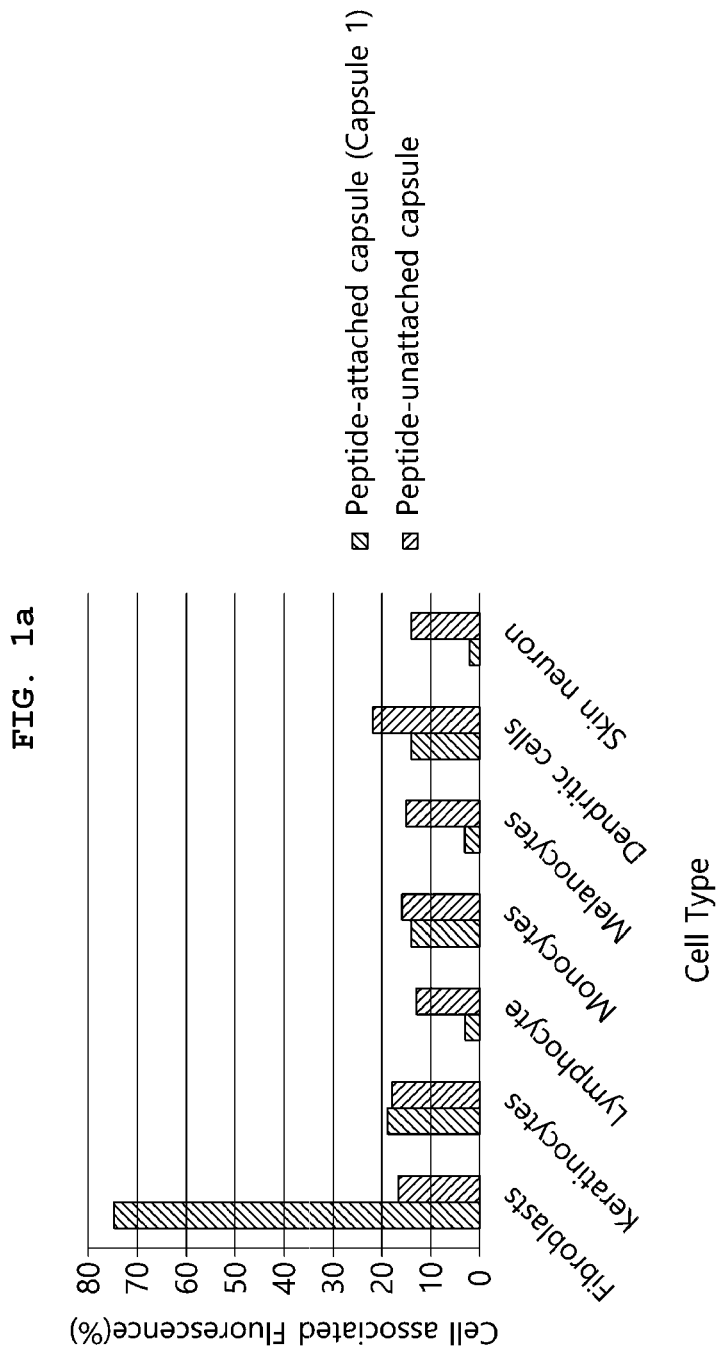

Hereinafter, a detailed description will be given of the present invention.

An aspect of the present invention pertains to a peptide having binding ability to cell-receptor, in which the peptide includes any one sequence of SEQ ID NOS: 1 to 3.

As used herein, the term "binding ability to cell-receptor" means the ability to bind to receptors formed on cells.

The amino acid sequences of the peptides of SEQ ID NOS: 1 to 3 are shown in Table 1 below.

TABLE 1

| SEQ ID NO: | Amino acid sequence |
|---|---|
| 1 | Ala-Lys-Ser-Thr |
| 2 | Glu-Gly-His-Lys-Ile-Phe-Pro-Ser-Trp-Tyr |
| 3 | Ala-Asp-Gly-Ser-Pro |

In Table 1, Ala represents alanine, Asp represents aspartic acid, Glu represents glutamic acid, Gly represents glycine, His represents histidine, Ile represents isoleucine, Lys represents lysine, Phe represents phenylalanine, Pro represents proline, Ser represents serine, Trp represents tryptophan, Tyr represents tyrosine, and Thr represents threonine.

In one aspect, cells targeted by the peptide may include melanocytes, keratinocytes or fibroblasts.

Also, the cell receptor may include a fibroblast growth factor receptor, an integrin receptor or a melanocortin receptor. Specifically, the melanocortin receptor may be a melanocortin 1 receptor (MC1R).

In an exemplary embodiment, the peptide of SEQ ID NO: 1 targets fibroblasts, and may bind to a fibroblast growth factor receptor.

Also, in an exemplary embodiment, the peptide of SEQ ID NO: 2 targets melanocytes, and may bind to a melanocortin receptor.

Also, in an exemplary embodiment, the peptide of SEQ ID NO: 3 targets keratinocytes, and may bind to an integrin receptor, especially a beta-1 family integrin receptor.

In one aspect, the peptides do not bind to cells other than respective target cells or receptors thereof, and the binding affinity thereof is high. Therefore, when a predetermined component is linked to the peptide, high delivery efficiency thereof to the target can be expected.

Another aspect of the present invention pertains to a microcapsule including the peptide linked to the surface thereof. The peptide may be linked onto a microcapsule by binding a hydrophilic group on the microcapsule, for example, a carboxyl group, to an N-terminus on the peptide, but the linking method is not limited, and may be performed through various methods well-known to those skilled in the art.

The microcapsule may include a wide variety of polymers, examples of which include polymers, heat-sensitive polymers, light-sensitive polymers, magnetic polymers, pH-sensitive polymers, salt-sensitive polymers, chemically sensitive polymers, polymer electrolytes, polysaccharides, peptides, proteins and/or plastics, but are not limited thereto. Examples of the polymer include, but are not limited to, poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallylmethylammonium chloride) (PDADMAC), poly(pyrrole) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthalaldehyde) (PTHF), poly(hexyl viologen) (PHV), poly(L-lysine) (PLL), polyvinyl alcohol (PVA), poly(L-arginine) (PARG), and poly(lactic-co-glycolic acid) (PLGA).

In an exemplary embodiment, the capsule may be provided in the form of a bilayer, in which the outer layer may include polyvinyl alcohol and the inner layer may include poly(lactic-co-glycolic acid) (PLGA).

Also, the microcapsule may include at least one material capable of generating an effective neutral charge, a negative charge or a positive charge on the outer layer of the capsule. In some cases, the charge of the capsule may aid to prevent or promote aggregation or clustering of the particles.

In one aspect, the peptide may be included in a density of 0.1 to 10 peptides/$\mu m^2$ based on the total cross-sectional area of the microcapsule, and the density of the peptide is preferably 0.3 to 8 peptides/$\mu m^2$, and most preferably 0.4 to 7 peptides/$\mu m^2$. The density of the peptide may mean the number of peptide strands present per unit surface area of the microcapsule.

For example, if the density of the peptide on the microcapsule is less than 0.1 peptides/$\mu m^2$ or exceeds 10 peptides/$\mu m^2$, a skin-condition improvement effect similar to that of a microcapsule to which the peptide is not linked may result, and given the above density range, good binding affinity to target cells and active ingredient delivery efficiency may be manifested.

In one aspect, the microcapsule further includes an active ingredient encapsulated in the capsule, and the active ingredient may include at least one selected from the group consisting of amino acids, plant-derived proteins or hydrolysates thereof, and yeast ferments, lysates thereof or filtrates thereof. Also, the active ingredient encapsulated in the capsule may include various plant extracts and fruit extracts thereof. Specifically, the plant extract may include a *Narcissus tazetta* bulb extract, a *Leucojum aestivum* bulb extract, etc., and the fruit extract may include a *Hylocereus undatus* fruit extract.

Also, the amino acids are not limited, and may include arginine, alanine, glutamine, glycine, isoleucine, leucine, lysine, histidine, proline, tyrosine, serine, valine, phenylalanine, tryptophan, threonine, aspartic acid, and the like.

In an exemplary embodiment, the plant-derived protein may include a lupine protein, and the yeast may include *Pichia pastoris*. In an exemplary embodiment, the yeast ferment may be a *Pichia* ferment lysate filtrate.

In the above aspect, each of the plant-derived protein or the hydrolysate thereof, and the yeast ferment, the lysate thereof or the filtrate thereof may be contained in an amount of 0.0001 to 30 wt % based on the total weight of the active ingredient. If the amount thereof is less than 0.0001 wt %, the effects thereof may become insignificant. On the other hand, if the amount thereof exceeds 30 wt %, stability problems such as discoloration and odor problems may occur. Each of the plant-derived protein or the hydrolysate thereof, and the yeast ferment, the lysate thereof or the filtrate thereof is preferably contained in an amount of 0.01 to 30 wt %, more preferably 0.01 to 25 wt %, based on the total weight of the active ingredient.

The amino acids may be contained in an amount of 0.00001 to 0.1 wt %, preferably 0.0001 to 0.1 wt %, and more preferably 0.0001 to 0.05 wt %, and the plant extract or the fruit extract may be contained in an amount of 0.0001 to 30 wt %. Each of the plant extract and the fruit extract is preferably contained in an amount of 0.001 to 20 wt %, and most preferably 0.001 to 15 wt %.

If the amount of amino acids is less than 0.00001 wt %, the effects thereof may become insignificant. On the other hand, if the amount thereof exceeds 0.1 wt %, problems related to unstable viscosity of the resulting formulation may occur.

If the amount of the plant extract or the fruit extract is less than 0.0001 wt %, the effects thereof may become insignificant. On the other hand, if the amount thereof exceeds 30 wt %, problems related to discoloration, odor and unstable viscosity of the resulting formulation may occur.

When the amounts of the components listed above fall in the above ranges, it is possible to obtain excellent moisturizing, skin barrier enhancement, whitening, wrinkle reduction and skin elasticity improvement effects.

Still another aspect of the present invention pertains to a cosmetic composition containing the microcapsule. The composition may be used for moisturizing, skin barrier enhancement, whitening, wrinkle reduction or skin elasticity improvement.

In the present specification, "skin barrier enhancement" means promotion of differentiation of skin keratinocytes, thus strengthening the outermost layer of the skin to thereby improve the state of the skin.

In one aspect, the composition may promote the synthesis of keratin 1, keratin 5, keratin 10, keratin 14, filaggrin, loricrin, elastin, collagen and the like.

In one aspect, the amount of the microcapsule in the cosmetic composition may be 0.0001 to 30 wt %, preferably 0.001 to 20 wt %, and most preferably 0.01 to 10 wt %.

If the amount of the microcapsule in the cosmetic composition is less than 0.0001 wt %, the effects thereof are insignificant. On the other hand, if the amount thereof exceeds 30 wt %, the dispersibility of the capsule in the composition may decrease and the viscosity of the resulting cosmetic composition may be changed.

In the present specification, the microcapsule in which the active ingredient is blended in an optimal amount and is encapsulated is called "CellActive Code". Also, a variety of formulations, such as toners, ampoules, serums, eye creams, nourishing creams and lotions may be manufactured using the composition containing the microcapsule. Encapsulating the active ingredient in the microcapsule is called smart capsulation. Also, the technique of accurately delivering the composition containing the microcapsule (smart capsule) including the active ingredient encapsulated therein to target cells is called "CellActive Technology".

A better understanding of the present invention will be given through the following preparation examples and examples. These preparation examples and examples are merely set forth to illustrate the present invention but are not to be construed as limiting the scope of the present invention.

PREPARATION EXAMPLES

[Preparation Example 1] Preparation of Peptide

The peptides of SEQ ID NOS: 1 to 3 shown in Table 1 were synthesized through an FMOC solid-phase method using an automated synthesizer (PeptrEx-R48, Peptron, Daejeon, Korea). The peptides thus synthesized were purified and analyzed through reverse-phase high-performance liquid chromatography (HPLC) (Prominence LC-20AB, Shimadzu, Japan) using RP columns (Shiseido Capcell Pak), and identified using a mass spectrometer (HP 1100 Series LC/MSD, Hewlett-Packard, Roseville, USA).

[Preparation Example 2] Preparation of Microcapsule

[Preparation Example 2-1] Preparation of Peptide-Unattached Microcapsule

A lipid concentrate part (ceramide, cholesterol, hydrogenated lecithin) was placed in a separate dissolution tank and warmed to 70° C. and thus dissolved, and a hydrophilic bioactive material part (panthenol, raffinose, niacinamide, *Camellia sinensis* leaf water) was placed in a separate dissolution tank and warmed to 45° C. and thus dissolved. The lipid concentrate part prepared above was placed in a dissolution tank containing a lipid stabilizer part and agitated for 5 min at a speed of 1,500 rpm using an agitator at 50° C., and the hydrophilic bioactive material part was added thereto, agitated for 5 min at a speed of 1,500 rpm using an agitator and homogenized, thus preparing a first concentrate phase in which the excess of hydrophilic active ingredient was bulkily homogenized. Moreover, the first concentrate phase was agitated for 1 hour at a low speed of 500 rpm using an agitator at 50° C., whereby the first concentrate phase was sufficiently hydrated. The first concentrate phase thus hydrated was placed in a high-pressure emulsifying machine at 50° C. and treated two times at a pressure of 9,000 bar, thereby forming a second concentrate phase in which the excess of hydrophilic bioactive material was positioned in the aqueous phase formed between the innermost aqueous phase and the lipid bilayer and was concentrated and encapsulated to a nano size. The second concentrate phase was then cooled to 28° C. with gentle agitation at a speed of 500 rpm using an agitator and thus stabilized, thereby manufacturing a peptide-unbound microcapsule. The diameter of the microcapsule thus manufactured was about 0.2 micrometer.

[Preparation Example 2-2] Preparation of Peptide-Attached Microcapsule

The peptide of Preparation Example 1 was attached to the microcapsule manufactured in Preparation Example 2-1.

The peptide of Preparation Example 1 was attached to the surface of the microcapsule by linking the N-terminus of the peptide to the carboxyl group on the surface of the peptide-unbound microcapsule. Specifically, the peptide-unbound microcapsule was resuspended in a MES (2-(N-morpholino) ethanesulfonic acid) buffered saline (pH 5.5) and allowed to react with EDAC (1-ethyl-3-(3-dimethylaminopropyl)carbodiimide) and NHS (N-hydroxysuccinimide) for about 1 hr. Thereafter, the microcapsule was centrifuged at about 15000 rpm for about 1 hour, thus removing EDAC and NHS to thereby activate the surface of the peptide-unbound microcapsule. Thereafter, the microcapsule was suspended in about 100 ml of PBS (phosphate-buffered saline), and was then allowed to react with about 0.1 g of the peptide of SEQ ID NO: 1 at room temperature. Thereafter, unreacted peptide was removed through washing with a PBS buffer. The peptide-linked microcapsules were manufactured using the peptides of SEQ ID NOS: 2 and 3 in the same manner as above, with the exception that the amounts of reagents that were added were adjusted. Whether the peptide was attached onto the microcapsule was evaluated through a Kaiser test. Additionally, the peptide density on the surface of the microcapsule was measured to be about 2 peptides/$\mu m^2$ using a scanning electron microscope (JSM-7100F).

The microcapsule to which the peptide of SEQ ID NO: 1 was linked was referred to as capsule 1, the microcapsule to which with the peptide of SEQ ID NO: 2 was linked was referred to as capsule 2, and the microcapsule to which the peptide of SEQ ID NO: 3 was linked was referred to as capsule 3.

[Preparation Example 3] Control of Peptide Density on Microcapsule

A microcapsule was manufactured in the same manner as in Preparation Example 2, with the exception that the amount of the peptide that was added and the peptide density on the microcapsule were adjusted. The experimental groups were divided as follows depending on the density.

TABLE 2

| Experimental group | Capsule 1-1 | Capsule 1-2 | Capsule 1-3 | Capsule 1-4 | Capsule 1-5 | Capsule 1-6 |
|---|---|---|---|---|---|---|
| | Capsule 2-1 | Capsule 2-2 | Capsule 2-3 | Capsule 2-4 | Capsule 2-5 | Capsule 2-6 |

TABLE 2-continued

| Peptide density | Capsule 3-1 | Capsule 3-2 | Capsule 3-3 | Capsule 3-4 | Capsule 3-5 | Capsule 3-6 |
|---|---|---|---|---|---|---|
| | 0.05 peptides/ $\mu m^2$ | 0.1 peptides/ $\mu m^2$ | 2 peptides/ $\mu m^2$ | 7 peptides/ $\mu m^2$ | 10 peptides/ $\mu m^2$ | 10.5 peptides/ $\mu m^2$ |

EXAMPLES

[Example 1] Cytotoxicity Test

B16 melanoma cells were treated with 10 μM of each of capsules 1 to 3, and cell viability was evaluated. A control group was treated with kojic acid and arbutin. As a result, the cell viability was hardly changed upon treatment with the capsule of the present invention, indicating that there was no cytotoxicity.

[Example 2] Binding Selectivity Test with Target Cells

In order to evaluate whether capsules 1 to 3 were able to bind to cells other than respective target cells, binding to various types of cells was measured. As a result, it was confirmed that capsules 1 to 3 hardly bound to cells other than respective target cells.

[Example 2-1] Capsule 1

The binding affinity of capsule 1 to cells was evaluated using flow cytometry (FACS) through fluorescence immunoassay. The cells used were fibroblasts, keratinocytes, lymphocyte, monocytes, melanocytes, dendritic cells and skin neuron. Based on the results of measurement, the binding rate of capsule 1 to fibroblasts, which are target cells, was about 75%, but the binding affinity thereof to cells other than the target cells was very low (FIG. 1a).

[Example 2-2] Capsule 2

Figure 1B:
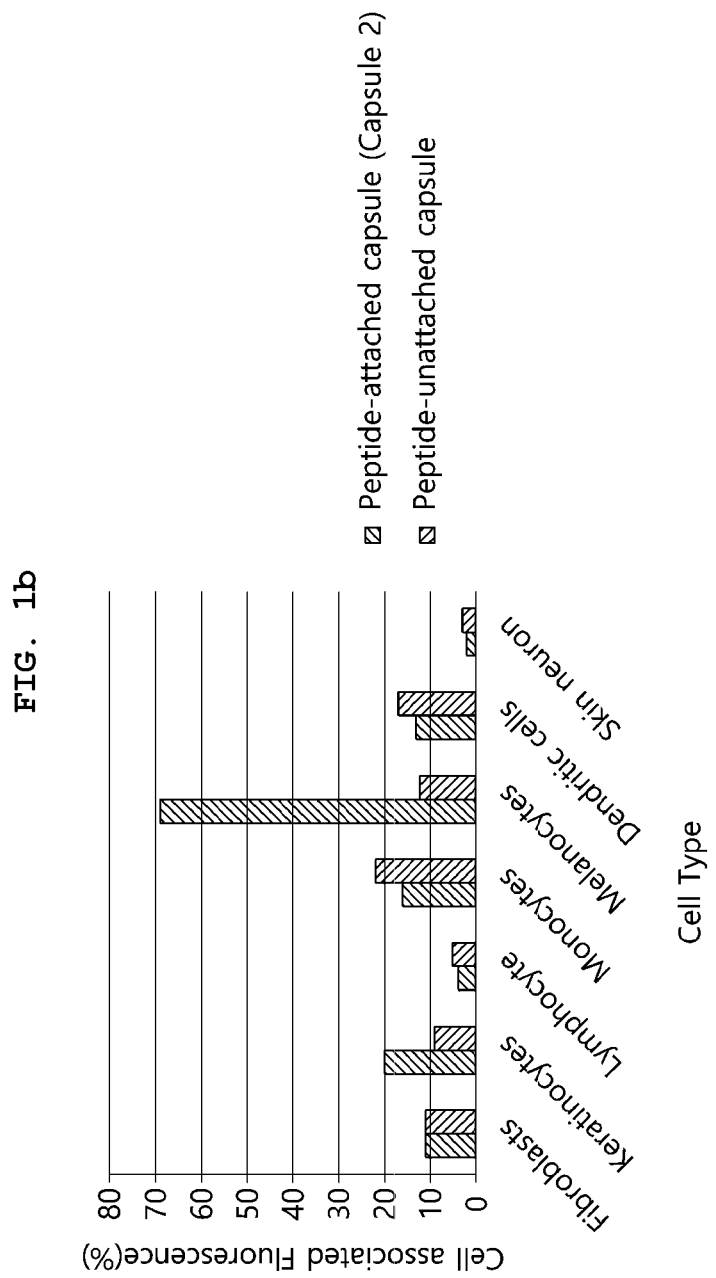

Capsule 2 was tested in the same manner as in Example 2-1. As a result, the binding affinity of capsule 2 to melanocytes, as target cells, was about 70%, but the binding rate thereof to other cells was very low (FIG. 1b).

[Example 2-3] Capsule 3

Capsule 3 was tested in the same manner as in Example 2-3. As a result, the binding rate of capsule 3 to keratinocytes, as target cells, was about 85%, but the binding rate thereof to other cells was very low (FIG. 1c).

[Example 3] Anti-Aging Effect of Peptide-Linked Microcapsule (Capsule 1-3)

[Example 3-1] Binding Affinity of Fibroblast and Capsule (Comparison of Binding Affinity Depending on Presence or Absence of Peptide)

The binding affinity of the microcapsule, the surface of which was linked with the peptide, and the microcapsule, the surface of which was not linked with the peptide, to fibroblasts and the absorption ability of the active ingredient were compared.

The binding process was delayed by culturing capsule 1 and target cells together at 4° C. for 1 hour, after which the binding affinity of the microcapsule, the surface of which was linked with the peptide, and the microcapsule, the surface of which was not linked with the peptide, to fibroblasts was measured. The binding affinity of capsule 1 to fibroblasts was as high as about 4 times the binding affinity of the microcapsule to which the peptide was not linked.

[Example 3-2] Comparison of Collagen and Elastin Production

The microcapsule, the surface of which was linked with the peptide, was reacted with fibroblasts, and the amounts of elastin and collagen that were produced were measured.

When using the capsule to which the peptide was not linked, the amount of collagen that was produced was insignificant, but when using capsule 1, to which the peptide was linked, the production of collagen type 1 and type 3 was increased by at least about 1.7 times compared to the capsule to which the peptide was not linked (FIGS. 2a and 2b).

Figure 2C:
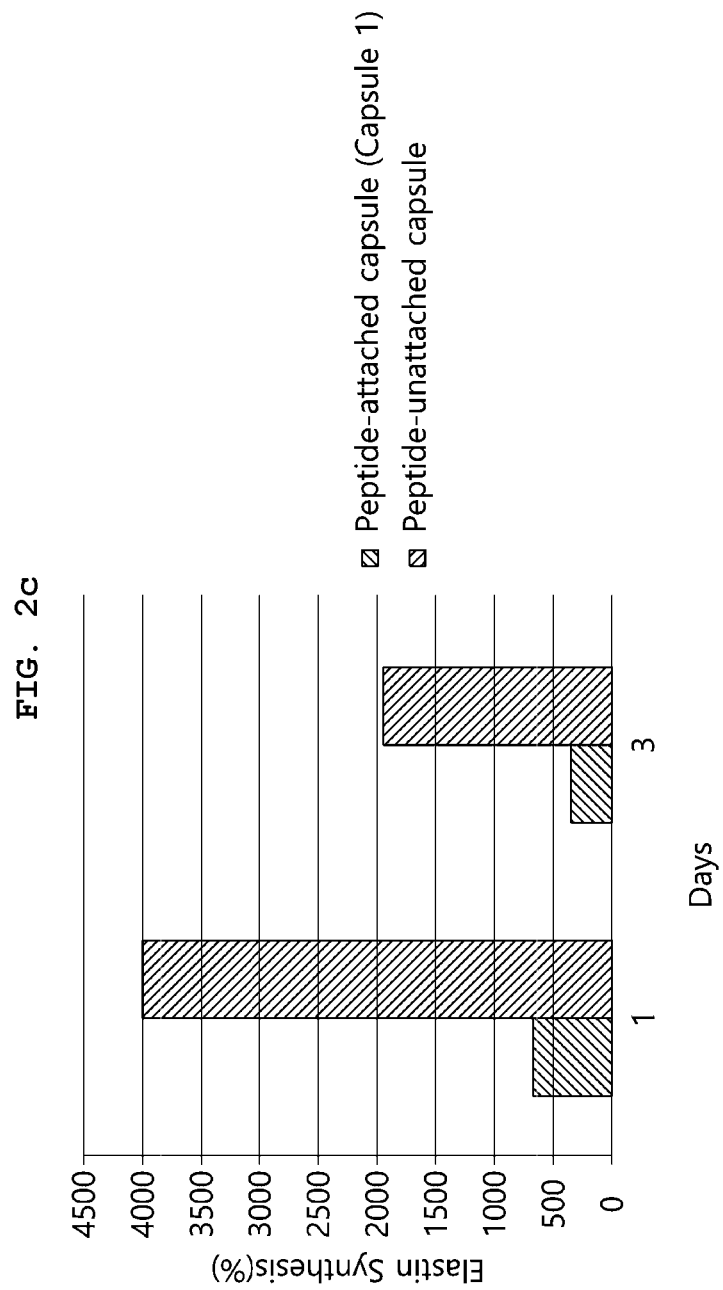

7 days after the capsule reaction, elastin production by a maximum of 9 times or more was exhibited when using capsule 1, to which the peptide was linked, compared to when using the capsule to which the peptide was not linked (FIG. 2c).

[Example 3-3] Panel Test for Skin Wrinkle Reduction

Figure 3:
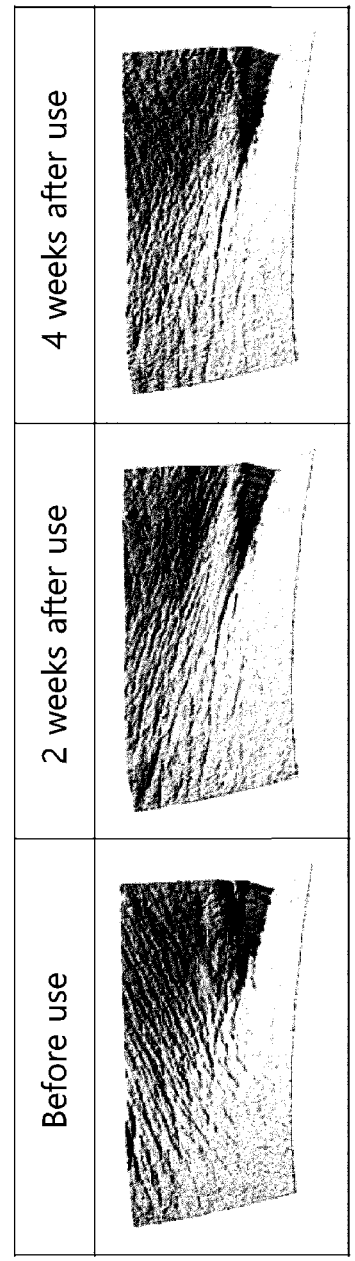
FIG. 3 shows the effect of reducing wrinkles around the eyes after using an ampoule containing the capsule of the present invention.

An ampoule containing 30 wt % of capsule 1 based on the total weight thereof was manufactured, and the ampoule was uniformly applied twice a day over the face of each of 21 females, from 35 to 65 years of age and free of skin disease, for 28 days, and the extent of reduction of wrinkles around the eyes was observed. As a result, an effect of reducing wrinkles around the eyes by about 10% was confirmed (FIG. 3).

[Example 4] Whitening Effect of Peptide-Linked Microcapsule (Capsule 2-3)

[Example 4-1] Binding Interference of Melanocyte and Alpha-MSH

Figure 4A:
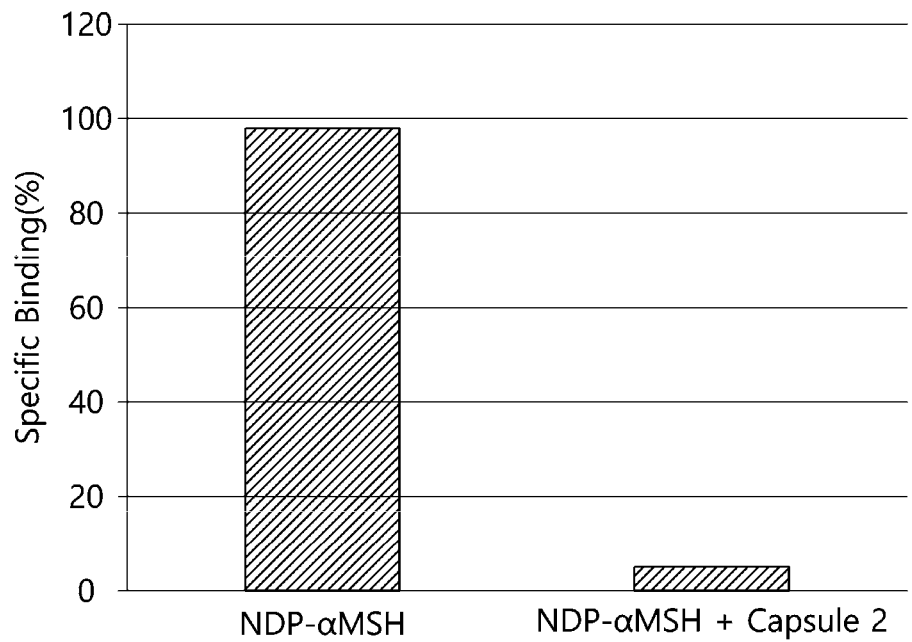
FIGS. 4a and 4b show the ability of binding interference of alpha-MSH (FIG. 4a) and ability of melanin synthesis inhibition (FIG. 4b) upon treatment with the capsule (capsule 2) of the present invention.

After treatment with 10 μM of each of the microcapsule, the surface of which was linked with the peptide (capsule 2), and the microcapsule, the surface of which was not linked with the peptide, the binding affinity between melanocyte and alpha-melanocyte stimulating hormone (MSH) was measured. As a result, when using capsule 2, it was found that the binding affinity of melanocyte and alpha-MSH was reduced by 95% or more (FIG. 4a).

[Example 4-2] Melanin Synthesis Inhibition Ability

Figure 4B:
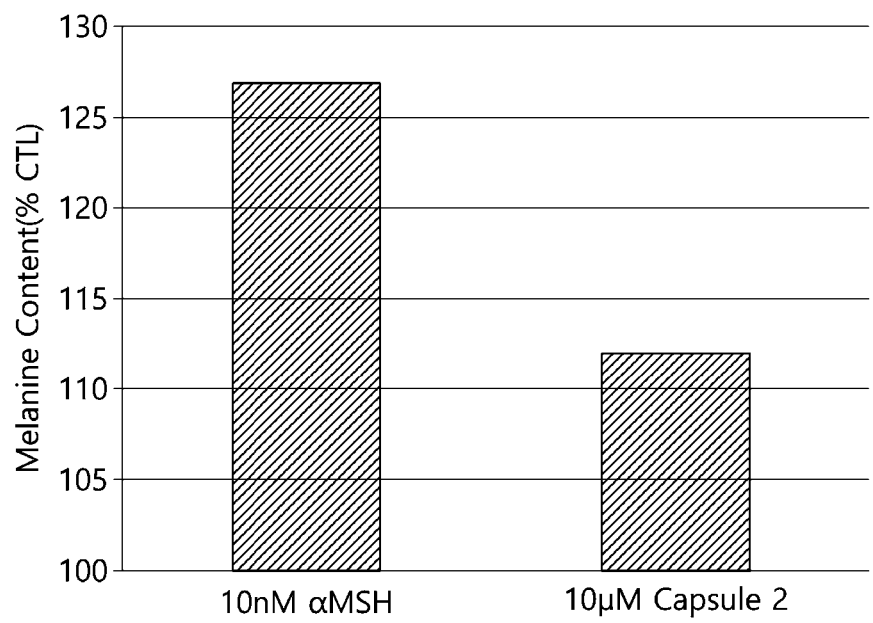

After treatment with 10 μM of each of the microcapsule, the surface of which was linked with the peptide, and the microcapsule, the surface of which was not linked with the peptide, the amounts of melanin that was synthesized were compared. As a result, when capsule 2 was administered, it was found that the production of melanin from melanocytes was greatly reduced (FIG. 4b).

[Example 4-3] Panel Test for Skin-Whitening Effect

Figure 5:
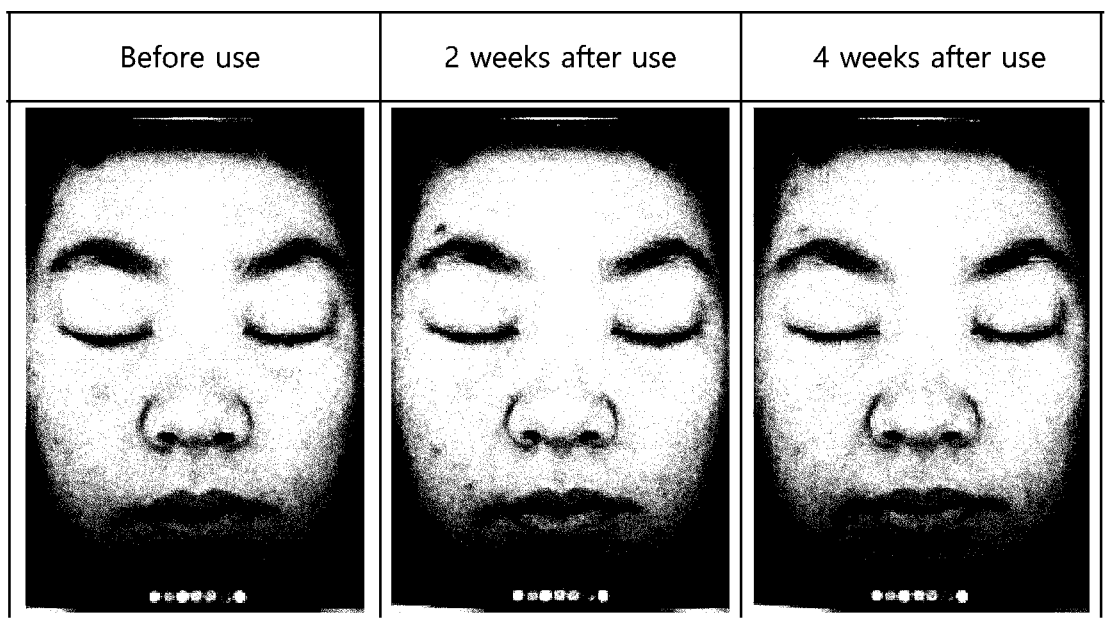
FIG. 5 shows the whitening effect after using a toner containing the capsule of the present invention.

A toner containing 15% of capsule 2 was uniformly applied twice a day over the face of each of 21 females, from 35 to 55 years of age and free of skin disease, for 14 days, and the whitening effect was evaluated. As a result, when the toner containing capsule 2 was applied, a significantly improved whitening effect was confirmed (FIG. 5).

[Example 5] Skin Barrier Improvement Effect of Peptide-Linked Microcapsule (Capsule 3-3)

[Example 5-1] Keratin 1, and Keratin 5 and Expression Enhancement Effect

Figure 6B:
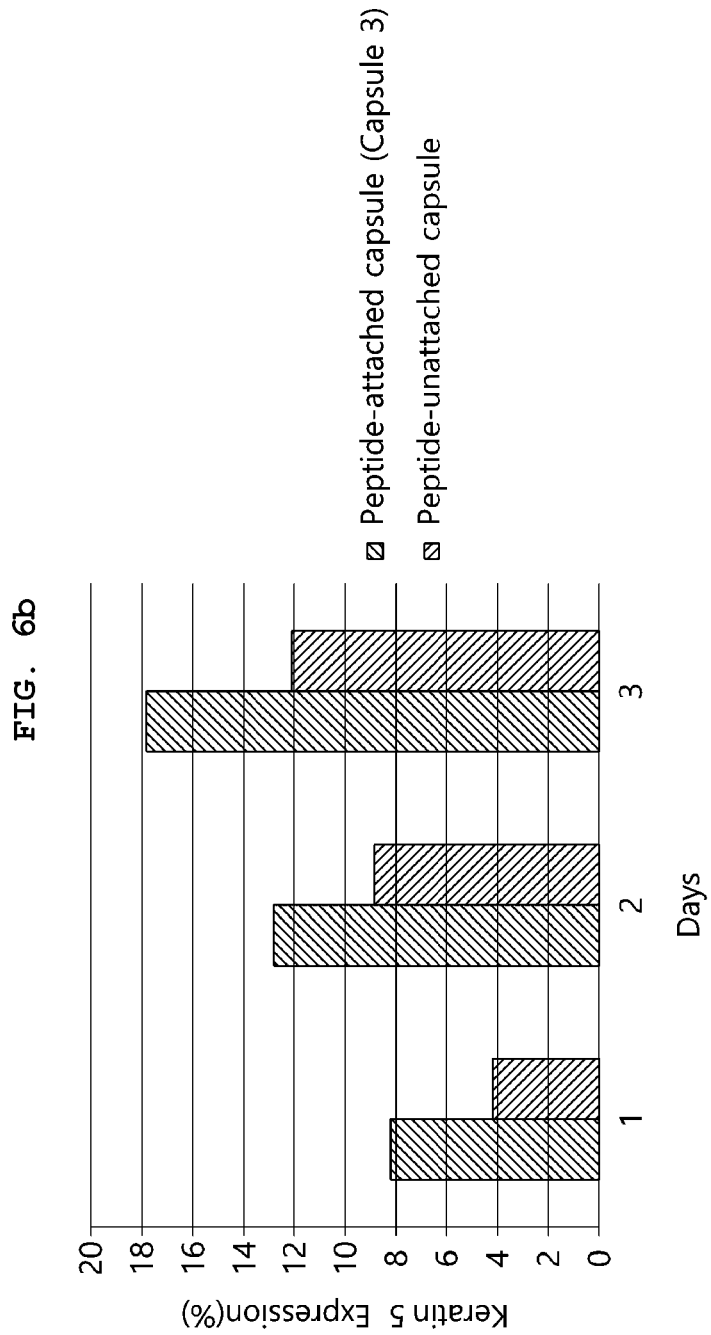

In order to evaluate the skin barrier improvement effect of capsule 3, to which the peptide was linked, the expression enhancement effect of keratin was measured. After treatment with 10 μM of each of the microcapsule, the surface of which was linked with the peptide, and the microcapsule, the surface of which was not linked with the peptide, the extent of expression of the above factors was measured. As a result, the amounts of keratin 1 and keratin 5 that were expressed were increased by about two times when using capsule 3 compared to when using the capsule to which the peptide was not linked (FIGS. 6a and 6b, in sequence).

[Example 5-2] Filaggrin Synthesis Enhancement Effect

Capsule treatment was performed in the same manner as in Example 5-1, and the filaggrin synthesis effect was measured. As a result, filaggrin expression by about 5 times was confirmed when using capsule 3 compared to when using the capsule to which the peptide was not linked (FIG. 6c).

[Example 6] Panel Test for Skin Barrier Enhancement Effect

Figure 7:
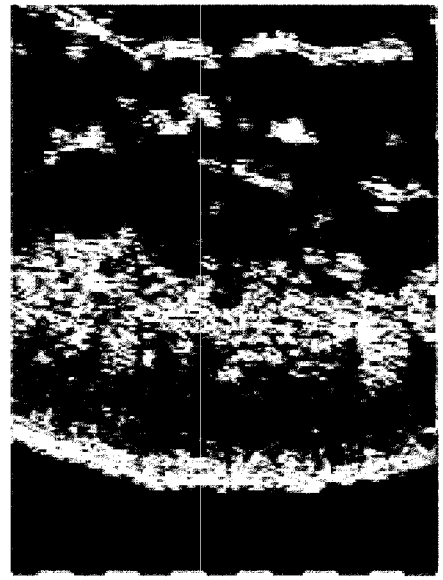
FIG. 7 shows the effect of improving the skin barrier (dermal density, skin thickness) after using a nourishing cream containing the capsule of the present invention.
Figure 7:
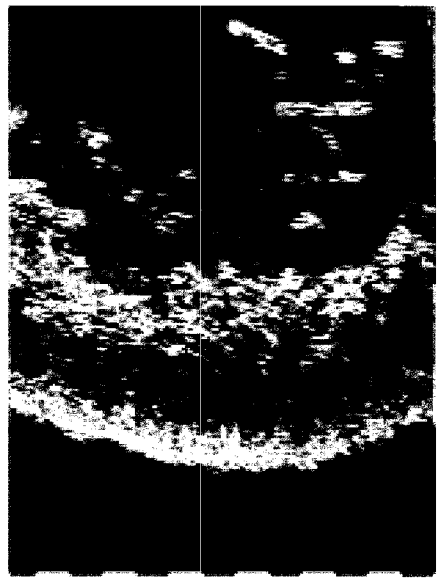
Figure 8:
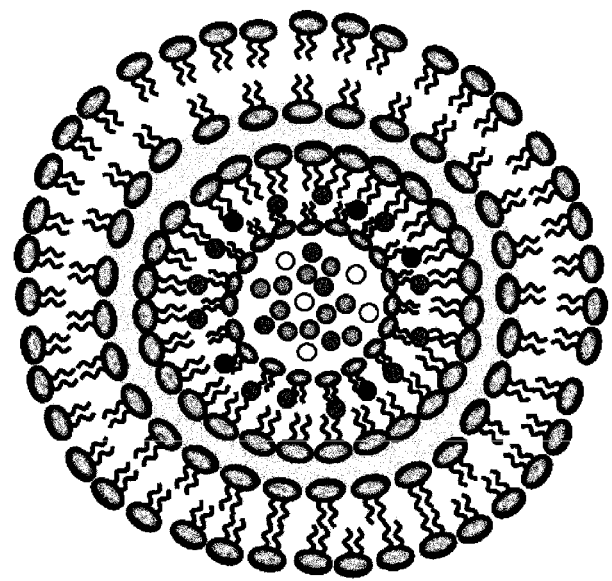
FIG. 8 schematically shows a microcapsule of the present invention configured such that an excess of hydrophilic bioactive material is stabilized in a multilayer structure composed of a lipid part.
Figure 9:
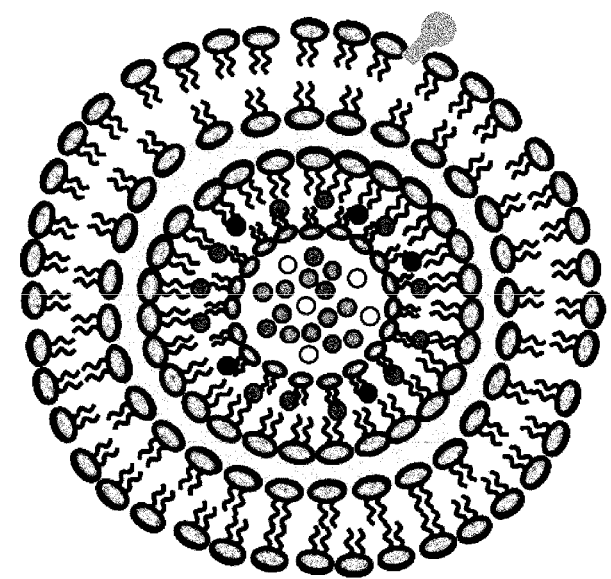
FIG. 9 schematically shows a microcapsule including the peptide.
Figure 10:
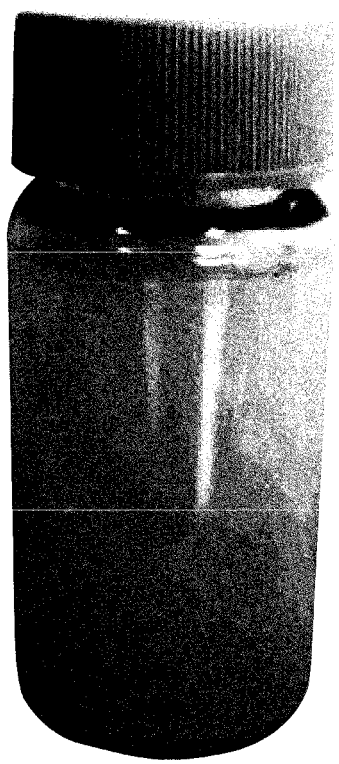
FIG. 10 is a photograph showing a concentrated composition sample manufactured through a smart capsulation process of the present invention.

A nourishing cream containing 20% of capsule 3 was uniformly applied twice a day over the face of each of 20 females, from 35 to 55 years of age and free of skin disease, for 14 days, and the skin dermal density and skin thickness were measured. As a result, when the nourishing cream containing capsule 3 was applied, the dermal density and skin thickness were significantly improved, and thus the skin barrier improvement effect was confirmed (FIG. 7).

[Example 7] Effect Difference Depending on Peptide Density

The experimental groups shown in Table 2 were tested as in Examples 3 to 6. The effect of using capsules 1-3, 2-3 and 3-3 (peptide density: 2 peptides/μm$^2$) was determined to be 10, and the results of individual experimental groups were represented as values relative to the capsules 1-3, 2-3 and 3-3.

Table 3 below shows the experimental results corresponding to the experiment of Example 3, Table 4 below shows the experimental results corresponding to Example 4, and Table 5 below shows the experimental results corresponding to Example 6.

TABLE 3

| Experimental group | Capsule 1-1 | Capsule 1-2 | Capsule 1-3 | Capsule 1-4 | Capsule 1-5 | Capsule 1-6 | Peptide-unlinked capsule |
|---|---|---|---|---|---|---|---|
| Binding affinity to fibroblasts | 2 | 7 | 10 | 9.5 | 7.5 | 3.5 | 1 |
| Collagen production | 1.5 | 7.5 | 10 | 9 | 7 | 3.5 | 1 |
| Elastin production | 2.5 | 8 | 10 | 9 | 7 | 3.5 | 1 |
| Skin wrinkle reduction and elasticity improvement | 1.5 | 6.5 | 10 | 9 | 8 | 3 | 1 |

TABLE 4

| Experimental group | Capsule 2-1 | Capsule 2-2 | Capsule 2-3 | Capsule 2-4 | Capsule 2-5 | Capsule 2-6 | Peptide-unlinked capsule |
|---|---|---|---|---|---|---|---|
| Binding interference of melanocyte and alpha-MSH | 3 | 7.5 | 10 | 10 | 7 | 3 | 1 |
| Melanin synthesis inhibition | 2 | 8 | 10 | 9 | 7.5 | 3.5 | 1 |
| Skin whitening | 2.5 | 8.5 | 10 | 9 | 7 | 3 | 1 |

TABLE 5

| Experimental group | Capsule 3-1 | Capsule 3-2 | Capsule 3-3 | Capsule 3-4 | Capsule 3-5 | Capsule 3-6 | Peptide-unlinked capsule |
|---|---|---|---|---|---|---|---|
| Keratin expression | 3.5 | 6.5 | 10 | 10 | 7.5 | 3 | 1 |
| Filaggrin synthesis | 2 | 5 | 10 | 9.5 | 7 | 2.5 | 1 |
| Skin barrier improvement | 3.5 | 6.5 | 10 | 8 | 7.5 | 2 | 1 |

As a result, when the peptide density fell out of the range of 0.1 to 10 peptides/μm$^2$, the skin-condition enhancement effect was found to be insignificant.

FORMULATION EXAMPLE

[Formulation Example 1] Toner (for Brightening)

TABLE 6

| | Component | Amount (wt %) |
|---|---|---|
| Active ingredient in capsule | Hydrolyzed lupine protein | 1.5 |
| | *Pichia* ferment lysate filtrate | 1.5 |
| | *Hylocereus undatus* fruit extract | 12.0 |
| | Amino acids (glutamic acid, glycine, histidine, lysine, isoleucine, phenylalanine, proline, serine, tryptophan, tyrosine) | 0.0015 |

TABLE 6-continued

| | Component | Amount (wt %) |
|---|---|---|
| Other ingredients | Water-soluble moisturizer | 20.0 |
| | Niacinamide | 2.0 |
| | Bifida ferment lysate | 3.0 |
| | Microemulsion (hydrogenated lecithin, ceramide NP, tocopheryl acetate, cholesterol, caprylic/capric triglyceride, *Camellia sinensis* leaf water, polyol) | 5.0 |
| | Mixture of *Ocimum basilicum* flower/leaf extract, *Pyrus malus* fruit water, *Houttuynia cordata* extract, *Chamomilla recutita* flower extract, *Althaea officinalis* leaf/root extract, *Lavandula angustifolia* flower/leaf/stem extract, *Rosmarinus officinalis* extract, *Foeniculum vulgare* leaf extract | 10.0 |
| | *Camellia sinensis* leaf water and other stabilizers | TO 100 |

[Formulation Example 2] Ampoule (for Anti-Aging)

TABLE 7

| | Component | Amount (wt %) |
|---|---|---|
| Active ingredient in capsule | Oligopeptide-1 | 0.001 |
| | Hydrolyzed lupine protein | 3.0 |
| | *Pichia* ferment lysate filtrate | 3.0 |
| | *Leucojum aestivum* bulb extract | 26.0 |
| | Amino acids (alanine, lysine, serine, threonine) | 0.003 |
| Other ingredients | Water-soluble moisturizer | 25.0 |
| | Palmitoyl pentapeptide-4 | 0.001 |
| | Bisabolol | 0.5 |
| | Niacinamide | 2.0 |
| | Adenosine | 0.04 |
| | Carnosine | 0.5 |
| | *Bellis perennis* flower extract | 1.0 |
| | Cholesteric liquid crystal (dihydrocholesteryl butyrate & dihydrocholesteryl oleate & cholesteryl butyrate & phytosteryl oleate) | 1.0 |
| | *Camellia sinensis* leaf water and other stabilizers | TO 100 |

[Formulation Example 3] Serum (for Anti-Aging)

TABLE 8

| | Component | Amount (wt %) |
|---|---|---|
| Active ingredient in capsule | Oligopeptide-1 | 0.001 |
| | Hydrolyzed lupine protein | 2.0 |
| | *Pichia* ferment lysate filtrate | 2.0 |
| | *Leucojum aestivum* bulb extract | 16.0 |
| | Amino acids (alanine, lysine, serine, threonine) | 0.002 |
| Other ingredients | Hydrogenated lecithin | 4.0 |
| | Oil-soluble emollient | 20.0 |
| | Water-soluble moisturizer | 10.0 |
| | Tocopheryl acetate | 1.0 |
| | Adenosine | 0.04 |
| | Mixture of *Ocimum basilicum* flower/leaf extract & *Pyrus malus* fruit water & *Houttuynia cordata* extract & *Chamomilla recutita* flower extract & *Althaea officinalis* leaf/root extract & *Lavandula angustifolia* flower/leaf/stem extract & *Rosmarinus officinalis* extract & | 10.0 |

TABLE 8-continued

| | Component | Amount (wt %) |
|---|---|---|
| | *Foeniculum vulgare* leaf extract | |
| | Palmitoyl pentapeptide-4 | 0.001 |
| | *Camellia sinensis* leaf water and other stabilizers | TO 100 |

[Formulation Example 4] Eye Cream (for Anti-Aging)

TABLE 9

| | Component | Amount (wt %) |
|---|---|---|
| Active ingredient in capsule | Oligopeptide-1 | 0.001 |
| | Hydrolyzed lupine protein | 2.0 |
| | *Pichia* ferment lysate filtrate | 2.0 |
| | *Leucojum aestivum* bulb extract | 16.0 |
| | Amino acids (alanine, lysine, serine, threonine) | 0.002 |
| Other ingredients | Oil-soluble emollient | 25 |
| | Water-soluble moisturizer | 15 |
| | Niacinamide | 2.0 |
| | Adenosine | 0.04 |
| | Sodium hyaluronate | 0.1 |
| | Palmitoyl pentapeptide-4 | 0.001 |
| | Tocopheryl acetate | 0.2 |
| | *Camellia sinensis* leaf water and other stabilizers | TO 100 |

[Formulation Example 5] Lotion (for Skin Elasticity)

TABLE 10

| | Component | Amount (wt %) |
|---|---|---|
| Active ingredient in capsule | Hydrolyzed lupine protein | 1.0 |
| | *Pichia* ferment lysate filtrate | 1.0 |
| | *Narcissus tazetta* bulb extract | 8.0 |
| | Amino acids (alanine, aspartic acid, glycine, serine, proline) | 0.001 |
| Other ingredients | Oil-soluble emollient | 15.0 |
| | Water-soluble moisturizer | 13.0 |
| | Tocopheryl acetate | 0.5 |
| | *Aloe barbadensis* leaf extract | 5.0 |
| | *Camellia sinensis* leaf water and other stabilizers | TO 100 |

[Formulation Example 6] Nourishing Cream (for Skin Elasticity)

TABLE 11

| | Component | Amount (wt %) |
|---|---|---|
| Active ingredient in capsule | Hydrolyzed lupine protein | 2.0 |
| | *Pichia* ferment lysate filtrate | 2.0 |
| | *Narcissus tazetta* bulb extract | 16.0 |
| | Amino acids (alanine, aspartic acid, glycine, serine, proline) | 0.002 |
| Other ingredients | Oil-soluble emollient | 20.0 |
| | Water-soluble moisturizer | 30.0 |
| | Palmitoyl pentapeptide-4 | 0.001 |
| | Bifida ferment lysate | 5.0 |

TABLE 11-continued

| Component | Amount (wt %) |
|---|---|
| Adenosine | 0.04 |
| Mixture of *Ocimum basilicum* flower/leaf extract & *Pyrus malus* fruit water & *Houttuynia cordata* extract & *Chamomilla recutita* flower extract & *Althaea officinalis* leaf/root extract & *Lavandula angustifolia* flower/leaf/stem extract & *Rosmarinus officinalis* extract & *Foeniculum vulgare* leaf extract | 10.0 |
| *Camellia sinensis* leaf water and other stabilizers | TO 100 |

SEQUENCE LIST FREE TEXT

SEQ ID NO: 1 (Ala-Lys-Ser-Thr) is the sequence of peptide that targets fibroblasts, and the peptide of SEQ ID NO: 1 is able to bind to a fibroblast growth factor receptor.

SEQ ID NO: 2 (Glu-Gly-His-Lys-Ile-Phe-Pro-Ser-Trp-Tyr) is the sequence of peptide that targets melanocytes, and the peptide of SEQ ID NO: 2 is able to bind to a melanocortin receptor.

SEQ ID NO: 3 (Ala-Asp-Gly-Ser-Pro) is the sequence of peptide that targets keratinocytes, and the peptide of SEQ ID NO: 3 is able to bind to an integrin receptor, especially a beta-1 family integrin receptor.

A sequence listing electronically submitted with the present application on Feb. 4, 2020 as an ASCII text file named 20200204_Q25620FR01_TU_SEQ, created on Feb. 3, 2020 and having a size of 1,000 bytes, is incorporated herein by reference in its entirety.

The invention claimed is:

1. A method for skin-moisturizing or enhancing skin barrier, the method comprising applying to a subject in need thereof an effective amount of a composition comprising a microcapsule comprising a peptide consisting of SEQ ID NO: 1 linked to a surface thereof.

2. The method of claim 1, wherein the peptide is contained in a density of 0.1 to 10 peptides/$\mu m^2$ based on a total cross-sectional area of the microcapsule.

3. The method of claim 1, wherein the microcapsule further comprises an active ingredient encapsulated in the capsule,
wherein the active ingredient comprises at least one selected from the group consisting of amino acids; a plant-derived protein or a hydrolysate thereof; a yeast ferment, a lysate thereof or a filtrate thereof; and a plant extract.

4. The method of claim 3, wherein the plant-derived protein comprises a lupine protein, and the yeast comprises *Pichia pastoris*.

5. The method of claim 3, wherein the amino acids are contained in an amount of 0.00001 to 0.1 wt % based on a total weight of the active ingredient, and each of the plant-derived protein or the hydrolysate thereof, the yeast ferment, the lysate thereof or the filtrate thereof, and the plant extract is contained in an amount of 0.0001 to 30 wt % based on the total weight of the active ingredient.

6. A microcapsule comprising a peptide consisting of SEQ ID NO: 2 linked to a surface thereof.

7. The microcapsule of claim 6, wherein the peptide is contained in a density of 0.1 to 10 peptides/$\mu m^2$ based on a total cross-sectional area of the microcapsule.

8. The microcapsule of claim 6, further comprising an active ingredient encapsulated in the capsule,
wherein the active ingredient comprises at least one selected from the group consisting of amino acids; a plant-derived protein or a hydrolysate thereof; a yeast ferment, a lysate thereof or a filtrate thereof; and a plant extract.

9. The microcapsule of claim 8, wherein the plant-derived protein comprises a lupine protein, and the yeast comprises *Pichia pastoris*.

10. The microcapsule of claim 8, wherein the amino acids are contained in an amount of 0.00001 to 0.1 wt % based on a total weight of the active ingredient, and each of the plant-derived protein or the hydrolysate thereof, the yeast ferment, the lysate thereof or the filtrate thereof, and the plant extract is contained in an amount of 0.0001 to 30 wt % based on the total weight of the active ingredient.

11. A method for skin-whitening, the method comprising applying to a subject in need thereof an effective amount of a composition comprising the microcapsule of claim 6.

12. A method for reducing skin-wrinkling or improving skin elasticity, the method comprising applying to a subject in need thereof an effective amount of a composition comprising a microcapsule comprising a peptide consisting of SEQ ID NO: 3 linked to a surface thereof.

13. The method of claim 12, wherein the peptide is contained in a density of 0.1 to 10 peptides/$\mu m^2$ based on a total cross-sectional area of the microcapsule.

14. The method of claim 12, wherein the microcapsule further comprises an active ingredient encapsulated in the capsule,
wherein the active ingredient comprises at least one selected from the group consisting of amino acids; a plant-derived protein or a hydrolysate thereof; a yeast ferment, a lysate thereof or a filtrate thereof; and a plant extract.

15. The method of claim 14, wherein the plant-derived protein comprises a lupine protein, and the yeast comprises *Pichia pastoris*.

16. The method of claim 14, wherein the amino acids are contained in an amount of 0.00001 to 0.1 wt % based on a total weight of the active ingredient, and each of the plant-derived protein or the hydrolysate thereof, the yeast ferment, the lysate thereof or the filtrate thereof, and the plant extract is contained in an amount of 0.0001 to 30 wt % based on the total weight of the active ingredient.

* * * * *